(12) United States Patent
Castro et al.

(10) Patent No.: US 7,691,401 B2
(45) Date of Patent: *Apr. 6, 2010

(54) POLY(BUTYLMETHACRYLATE) AND RAPAMYCIN COATED STENT

(75) Inventors: Daniel Castro, Santa Clara, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 539 days.

This patent is subject to a terminal disclaimer.

(21) Appl. No.: 11/132,048

(22) Filed: May 17, 2005

(65) Prior Publication Data

US 2005/0208098 A1 Sep. 22, 2005

Related U.S. Application Data

(60) Division of application No. 10/678,346, filed on Oct. 3, 2003, now Pat. No. 6,953,560, which is a continuation of application No. 09/676,049, filed on Sep. 28, 2000, now Pat. No. 6,716,444.

(51) Int. Cl.
A61F 2/04 (2006.01)

(52) U.S. Cl. ..................................... 424/426; 424/423

(58) Field of Classification Search .................. None
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,678,468 A | 7/1987 | Hiroyoshi |
| 4,733,665 A | 3/1988 | Palmaz |
| 4,800,882 A | 1/1989 | Gianturco |
| 4,816,339 A | 3/1989 | Tu et al. |

(Continued)

FOREIGN PATENT DOCUMENTS

DE 42 24 401 1/1994

(Continued)

OTHER PUBLICATIONS

U.S. Appl. No. 09/894,293, filed Jun. 27, 2001, Roorda.

(Continued)

*Primary Examiner*—Carlos A Azpuru
(74) *Attorney, Agent, or Firm*—Squire, Sanders & Dempsey, L.L.P.

(57) ABSTRACT

An implantable medical device, such as a stent, is disclosed. The device includes a substrate and a polymeric layer including poly(methylmethacrylate) or poly(butylmethacrylate) supported by the substrate. The polymeric layer contains rapamycin. A barrier is over at least a portion of the polymeric layer to reduce the rate of release of rapamycin from the implantable medical device. The polymeric layer can additionally include poly(ethylene co-vinyl acetate).

18 Claims, 3 Drawing Sheets

U.S. PATENT DOCUMENTS

| | | |
|---|---|---|
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,064,435 A | 11/1991 | Porter |
| 5,071,407 A | 12/1991 | Termin et al. |
| 5,078,736 A | 1/1992 | Behl |
| 5,092,841 A | 3/1992 | Spears |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,344,411 A | 9/1994 | Domb et al. |
| 5,344,425 A | 9/1994 | Sawyer |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,474,089 A | 12/1995 | Waynant |
| 5,485,496 A | 1/1996 | Lee et al. |
| 5,516,881 A | 5/1996 | Lee et al. |
| 5,569,463 A | 10/1996 | Helmus et al. |
| 5,571,086 A | 11/1996 | Kaplan et al. |
| 5,576,072 A | 11/1996 | Hostettler et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,662,960 A | 9/1997 | Hostettler et al. |
| 5,667,767 A | 9/1997 | Greff et al. |
| 5,670,558 A | 9/1997 | Onishi et al. |
| 5,674,242 A | 10/1997 | Phan et al. |
| 5,676,685 A | 10/1997 | Razavi |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,728,152 A | 3/1998 | Mirsch, II et al. |
| 5,735,897 A | 4/1998 | Buirge |
| 5,746,998 A | 5/1998 | Torchilin et al. |
| 5,759,205 A | 6/1998 | Valentini |
| 5,762,638 A | 6/1998 | Shikani et al. |
| 5,776,184 A | 7/1998 | Tuch |
| 5,783,657 A | 7/1998 | Pavlin et al. |
| 5,788,979 A | 8/1998 | Alt et al. |
| 5,792,550 A | 8/1998 | Phillips et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,830,430 A | 11/1998 | Unger et al. |
| 5,837,008 A | 11/1998 | Berg et al. |
| 5,837,313 A | 11/1998 | Ding et al. |
| 5,843,156 A | 12/1998 | Slepian et al. |
| 5,849,035 A | 12/1998 | Pathak et al. |
| 5,849,368 A | 12/1998 | Hostettler et al. |
| 5,849,859 A | 12/1998 | Acemoglu |
| 5,851,508 A | 12/1998 | Greff et al. |
| 5,854,376 A | 12/1998 | Higashi |
| 5,854,382 A | 12/1998 | Loomis |
| 5,855,563 A | 1/1999 | Kaplan et al. |
| 5,855,599 A | 1/1999 | Wan |
| 5,857,998 A | 1/1999 | Barry |
| 5,858,746 A | 1/1999 | Hubbell et al. |
| 5,858,990 A | 1/1999 | Walsh |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,895,420 A | 4/1999 | Mirsch, II et al. |
| 5,898,066 A | 4/1999 | Benowitz et al. |
| 5,899,935 A | 5/1999 | Ding |
| 5,902,875 A | 5/1999 | Roby et al. |
| 5,905,168 A | 5/1999 | Dos Santos et al. |
| 5,910,564 A | 6/1999 | Gruning et al. |
| 5,911,702 A | 6/1999 | Romley et al. |
| 5,914,387 A | 6/1999 | Roby et al. |
| 5,919,570 A | 7/1999 | Hostettler et al. |
| 5,919,893 A | 7/1999 | Roby et al. |
| 5,925,720 A | 7/1999 | Kataoka et al. |
| 5,932,299 A | 8/1999 | Katoot |
| 5,951,458 A | 9/1999 | Hastings et al. |
| 5,955,509 A | 9/1999 | Webber et al. |
| 5,958,385 A | 9/1999 | Tondeur et al. |
| 5,961,547 A | 10/1999 | Razavi |
| 5,962,007 A | 10/1999 | Cooper et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,005,020 A | 12/1999 | Loomis |
| 6,010,530 A | 1/2000 | Goicoechea |
| 6,011,125 A | 1/2000 | Lohmeijer et al. |
| 6,013,780 A | 1/2000 | Neufeld et al. |
| 6,015,541 A | 1/2000 | Greff et al. |
| 6,017,577 A | 1/2000 | Hostettler et al. |
| 6,022,901 A | 2/2000 | Goodman |
| 6,026,316 A | 2/2000 | Kucharczyk et al. |
| 6,028,164 A | 2/2000 | Loomis |
| 6,030,656 A | 2/2000 | Hostettler et al. |
| 6,033,582 A | 3/2000 | Lee et al. |
| 6,034,204 A | 3/2000 | Mohr et al. |
| 6,040,058 A | 3/2000 | Hostettler et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,938 A | 5/2000 | Unger et al. |
| 6,056,993 A | 5/2000 | Leidner et al. |
| 6,060,451 A | 5/2000 | DiMaio et al. |
| 6,060,518 A | 5/2000 | Kabanov et al. |
| 6,061,587 A | 5/2000 | Kucharczyk et al. |
| 6,080,488 A | 6/2000 | Hostettler et al. |
| 6,086,773 A | 7/2000 | Dufresne et al. |

| | | | | | | | |
|---|---|---|---|---|---|---|---|
| 6,096,070 | A | 8/2000 | Ragheb et al. | 6,346,110 | B2 | 2/2002 | Wu |
| 6,096,726 | A | 8/2000 | Opolski | 6,358,556 | B1 | 3/2002 | Ding et al. |
| 6,099,562 | A | 8/2000 | Ding et al. | 6,379,381 | B1 | 4/2002 | Hossainy et al. |
| 6,102,046 | A | 8/2000 | Weinstein et al. | 6,387,379 | B1 | 5/2002 | Goldberg et al. |
| 6,110,188 | A | 8/2000 | Narciso, Jr. | 6,391,052 | B2 | 5/2002 | Buirge |
| 6,110,483 | A | 8/2000 | Whitbourne et al. | 6,395,326 | B1 | 5/2002 | Castro et al. |
| 6,113,629 | A | 9/2000 | Ken | 6,410,044 | B1 | 6/2002 | Chudzik |
| 6,120,491 | A | 9/2000 | Kohn et al. | 6,419,692 | B1 | 7/2002 | Yang et al. |
| 6,120,536 | A | 9/2000 | Ding et al. | 6,451,373 | B1 | 9/2002 | Hossainy et al. |
| 6,120,788 | A | 9/2000 | Barrows | 6,482,834 | B2 | 11/2002 | Spada et al. |
| 6,120,904 | A | 9/2000 | Hostettler et al. | 6,494,862 | B1 | 12/2002 | Ray et al. |
| 6,121,027 | A | 9/2000 | Clapper et al. | 6,503,538 | B1 | 1/2003 | Chu et al. |
| 6,126,649 | A | 10/2000 | VanTassel et al. | 6,503,556 | B2 | 1/2003 | Harish et al. |
| 6,129,761 | A | 10/2000 | Hubbell | 6,503,954 | B1 | 1/2003 | Bhat et al. |
| 6,136,006 | A | 10/2000 | Johnson et al. | 6,506,437 | B1 | 1/2003 | Harish et al. |
| 6,136,333 | A | 10/2000 | Cohn et al. | 6,524,347 | B1 | 2/2003 | Myers et al. |
| 6,140,452 | A | 10/2000 | Felt et al. | 6,527,801 | B1 | 3/2003 | Dutta |
| 6,143,354 | A | 11/2000 | Koulik et al. | 6,527,863 | B1 | 3/2003 | Pacetti et al. |
| 6,153,252 | A | 11/2000 | Hossainy et al. | 6,528,526 | B1 | 3/2003 | Myers et al. |
| 6,156,064 | A | 12/2000 | Chouinard | 6,530,950 | B1 | 3/2003 | Alvarado et al. |
| 6,156,350 | A | 12/2000 | Constantz | 6,530,951 | B1 | 3/2003 | Bates et al. |
| 6,159,232 | A | 12/2000 | Nowakowski | 6,540,776 | B2 | 4/2003 | Sanders Millare et al. |
| 6,159,978 | A | 12/2000 | Myers et al. | 6,544,223 | B1 | 4/2003 | Kokish |
| 6,162,244 | A | 12/2000 | Braun et al. | 6,544,543 | B1 | 4/2003 | Mandrusov et al. |
| 6,165,212 | A | 12/2000 | Dereume et al. | 6,544,582 | B1 | 4/2003 | Yoe |
| 6,172,167 | B1 | 1/2001 | Stapert et al. | 6,555,157 | B1 | 4/2003 | Hossainy |
| 6,177,523 | B1 | 1/2001 | Reich et al. | 6,558,733 | B1 | 5/2003 | Hossainy et al. |
| 6,178,346 | B1 | 1/2001 | Amundson et al. | 6,565,659 | B1 | 5/2003 | Pacetti et al. |
| 6,179,817 | B1 | 1/2001 | Zhong | 6,572,644 | B1 | 6/2003 | Moein |
| 6,180,632 | B1 | 1/2001 | Myers et al. | 6,585,755 | B2 | 7/2003 | Jackson et al. |
| 6,183,469 | B1 | 2/2001 | Thapliyal et al. | 6,585,765 | B1 | 7/2003 | Hossainy et al. |
| 6,197,051 | B1 | 3/2001 | Zhong | 6,585,926 | B1 | 7/2003 | Mirzaee |
| 6,203,551 | B1 | 3/2001 | Wu | 6,605,154 | B1 | 8/2003 | Villareal |
| 6,211,247 | B1 | 4/2001 | Goodman | 6,616,765 | B1 | 9/2003 | Hossaony et al. |
| 6,211,249 | B1 | 4/2001 | Cohn et al. | 6,623,448 | B2 | 9/2003 | Slater |
| 6,214,901 | B1 | 4/2001 | Chudzik et al. | 6,625,486 | B2 | 9/2003 | Lundkvist et al. |
| 6,231,600 | B1 | 5/2001 | Zhong | 6,645,135 | B1 | 11/2003 | Bhat |
| 6,238,364 | B1 | 5/2001 | Becker | 6,645,195 | B1 | 11/2003 | Bhat et al. |
| 6,240,616 | B1 | 6/2001 | Yan | 6,656,216 | B1 | 12/2003 | Hossainy et al. |
| 6,245,753 | B1 | 6/2001 | Byun et al. | 6,656,506 | B1 | 12/2003 | Wu et al. |
| 6,245,760 | B1 | 6/2001 | He et al. | 6,660,034 | B1 | 12/2003 | Mandrusov et al. |
| 6,248,129 | B1 | 6/2001 | Froix | 6,663,662 | B2 | 12/2003 | Pacetti et al. |
| 6,249,952 | B1 | 6/2001 | Ding | 6,663,880 | B1 | 12/2003 | Roorda et al. |
| 6,251,136 | B1 | 6/2001 | Guruwaiya et al. | 6,673,154 | B1 | 1/2004 | Pacetti et al. |
| 6,254,632 | B1 | 7/2001 | Wu et al. | 6,673,385 | B1 | 1/2004 | Ding et al. |
| 6,254,634 | B1 | 7/2001 | Anderson et al. | 6,689,099 | B2 | 2/2004 | Mirzaee |
| 6,258,121 | B1 | 7/2001 | Yang et al. | 6,695,920 | B1 | 2/2004 | Pacetti et al. |
| 6,258,371 | B1 | 7/2001 | Koulik et al. | 6,706,013 | B1 | 3/2004 | Bhat et al. |
| 6,261,320 | B1 | 7/2001 | Tam et al. | 6,709,514 | B1 | 3/2004 | Hossainy |
| 6,262,034 | B1 | 7/2001 | Mathiowitz et al. | 6,712,845 | B2 | 3/2004 | Hossainy |
| 6,265,016 | B1 | 7/2001 | Hostettler et al. | 6,713,119 | B2 | 3/2004 | Hossainy et al. |
| 6,265,199 | B1 | 7/2001 | Sheppard et al. | 6,716,444 | B1 | 4/2004 | Castro et al. |
| 6,270,788 | B1 | 8/2001 | Koulik et al. | 6,723,120 | B2 | 4/2004 | Yan |
| 6,273,913 | B1 * | 8/2001 | Wright et al. ............... 623/1.42 | 6,733,768 | B2 | 5/2004 | Hossainy et al. |
| 6,274,164 | B1 | 8/2001 | Novich | 6,740,040 | B1 | 5/2004 | Mandrusov et al. |
| 6,277,449 | B1 | 8/2001 | Kolluri et al. | 6,743,462 | B1 | 6/2004 | Pacetti |
| 6,283,947 | B1 | 9/2001 | Mirzaee | 6,749,626 | B1 | 6/2004 | Bhat et al. |
| 6,283,949 | B1 | 9/2001 | Roorda | 6,753,071 | B1 | 6/2004 | Pacetti |
| 6,283,951 | B1 | 9/2001 | Flaherty et al. | 6,758,859 | B1 | 7/2004 | Dang et al. |
| 6,284,305 | B1 | 9/2001 | Ding et al. | 6,759,054 | B2 | 7/2004 | Chen et al. |
| 6,287,249 | B1 | 9/2001 | Tam et al. | 6,764,505 | B1 | 7/2004 | Hossainy et al. |
| 6,287,628 | B1 | 9/2001 | Hossainy et al. | 6,790,228 | B2 | 9/2004 | Hossainy et al. |
| 6,290,729 | B1 | 9/2001 | Slepian et al. | 6,861,088 | B2 | 3/2005 | Weber et al. |
| 6,299,604 | B1 | 10/2001 | Ragheb et al. | 6,865,810 | B2 | 3/2005 | Stinson |
| 6,302,875 | B1 | 10/2001 | Makower et al. | 6,869,443 | B2 | 3/2005 | Buscemi et al. |
| 6,306,176 | B1 | 10/2001 | Whitbourne | 6,878,160 | B2 | 4/2005 | Gilligan et al. |
| 6,306,177 | B1 | 10/2001 | Felt et al. | 6,887,270 | B2 | 5/2005 | Miller et al. |
| 6,316,522 | B1 | 11/2001 | Loomis et al. | 6,887,485 | B2 | 5/2005 | Fitzhugh et al. |
| 6,322,771 | B1 | 11/2001 | Linden et al. | 6,890,546 | B2 | 5/2005 | Mollison et al. |
| 6,331,313 | B1 | 12/2001 | Wong et al. | 6,899,731 | B2 | 5/2005 | Li et al. |
| 6,334,867 | B1 | 1/2002 | Anson | 6,953,560 | B1 * | 10/2005 | Castro et al. ................. 423/423 |
| 6,335,029 | B1 * | 1/2002 | Kamath et al. ............... 424/423 | 2001/0007083 | A1 | 7/2001 | Roorda |
| 6,344,035 | B1 | 2/2002 | Chudzik et al. | 2001/0014717 | A1 | 8/2001 | Hossainy et al. |

| | | |
|---|---|---|
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |

| | | |
|---|---|---|
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

U.S. Appl. No. 10/176,504, filed Jun. 21, 2002, Roorda et al.
U.S. Appl. No. 10/176,510, filed Jun. 21, 2002, Hossainy et al.
U.S. Appl. No. 10/177,117, filed Jun. 21, 2002, Hossainy.
U.S. Appl. No. 10/177,154, filed Jun. 21, 2002, Hossainy et al.
U.S. Appl. No. 10/198,912, filed Jul. 19, 2002, Ding et al.
U.S. Appl. No. 10/320,899, filed Dec. 16, 2002, Shah et al.
U.S. Appl. No. 10/428,691, filed May 1, 2003, Pacetti.
Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003, (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Atotech, *Pallatect™ A Process for Autocatalytic Deposition of Palladium*, http://www.insulectro.com/Pallatect.pdf, printed Mar. 17, 2004 (4 pages).
Atotech, *Atotech Global-Home*, http://www.atotech.com/start.php3?cl_my$_{13}$ id=30574, printed Mar. 17, 2004 (1 page).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Baudrand et al., *Electroless Palladium, Past and Future* Proceedings of the AESF annual technical conference American Electroplaters and Surface Finishers Society, 1999, pp. 49-51.
Chemical Business Newsbase, "*Headline: Modern Plastics International: New PET barrier technologies show promise in beer bottles*", Copyright 2000 FT Asia Intelligence Wire, Mar. 10, 2000 (1 page).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).

DNP Products & Services—Packaging, "Barrier Carton for Liquid L-Carton L-Barrier L-Alumi," http://www.dnp.co.jp/international/pack/carton/carton_1.html, printed Mar. 17, 2004 (1 page).
DNP Products & Services—Packaging, "Barrier Carton for Liquid L-Carton L-Barrier L-Alumi," http://www.dnp.co.jp/international/pack/carton/carton_2.html, printed Mar. 17, 2004 (2 pages).
DNP Products & Services—Packaging, "Barrier Carton for Liquid L-Carton L-Barrier L-Alumi," http://www.dnp.co.jp/international/pack/carton/carton_3.html, printed Mar. 17, 2004 (1 page).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Electro-Coatings of Iowa, Inc., "Kanigen® Electroless Nickel Alloy," http://www.platingforindustry.com/electrocoatings/kantech.htm, printed Mar. 17, 2004 (3 pages).
Erlat et al., *Morphology And Gas Barrier Properties Of Thin $SiO_x$ Coatings On Polycarbonate: Correlations With Plasma-Enhanced Chemical Vapor Deposition Conditions*, J. Mater. Res., vol. 15, No. 3, Mar. 2000, pp. 704-717.
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Mitsubishi Chemical Kohjin PAX Corporation, "Transparent Excellent Gas Barrier Plastic Film . . . Techbarrier®," http://www.techbarrier.com/techbarrier/index.htm, printed Mar. 17, 2004 (3 pages).
Mitsubishi Chemical Kohjin PAX Corporation, "Techbarrier®-S," http://www.techbarrier.com/techbarrier/tech-s.htm, printed Mar. 17, 2004 (2 pages).
Mitsubishi Chemical Kohjin PAX Corporation, "How to Handle and Convert Techbarrier®," http://www.techbarrier.com/techbarrier/tech-kakou.htm, printed Mar. 17, 2004 (2 pages).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Modern Plastics, *New PET Barrier Technologies Show Promise in Beer Bottle Advances to be on Tap At Industry Event*, http://www.modplas.com/news/month_0100/gr01.htm, printed Dec. 3, 2002 (6 pages).
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pharmaceutical & Medical Packaging News, "Film Preserves Blood Substitute," http://www.devicelink.com/grabber.php3?URL=http:www.devicelink.com/pmpn/achive, printed Dec. 10, 2003 (3 pages).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

U.S. Appl. No. 10/376,348, filed Feb. 26, 2003, Ding et al.

\* cited by examiner

POLY(BUTYLMETHACRYLATE) AND RAPAMYCIN COATED STENT

CROSS REFERENCE

This is a divisional application of U.S. patent application Ser. No. 10/678,346 filed Oct. 3, 2003, now U.S. Pat. No. 6,953,560 which is a continuation of U.S. patent application Ser. No. 09/676,049 filed Sep. 28, 2000 now U.S. Pat. No. 6,716,444. This divisional application claims the priority benefit of U.S. patent application Ser. No. 10/678,346, filed Oct. 3, 2000, now abandoned, and U.S. patent application Ser. No. 09/676,049 filed Sep. 22, 2000, now U.S. Pat. No. 6,716,444, and this divisional application hereby incorporates by reference the complete contents of these applications.

BACKGROUND OF THE INVENTION

1. Field of the Invention

The present invention relates to implantable medical devices that release a drug.

2. Description of the Background

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the arterial lumen. The balloon is then deflated to a smaller profile to allow the catheter to be withdrawn from the patient's vasculature.

In treating the damaged vasculature tissue, and to deter thrombosis and restenosis, drugs are commonly administered to the treatment site. For example, anticoagulants are commonly used to prevent thrombosis of the coronary lumen. Antiplatelets are administered to reduce the incidence of major adverse cardiac events. Cytostatic agents are presently used in clinical trials to reduce post-angioplasty proliferation of the vascular tissue.

Systemic administration of such drugs in sufficient amounts to supply an efficacious concentration to the local treatment site often produces adverse or toxic side effects for the patient. Accordingly, local delivery is a preferred method of treatment since smaller amounts of medication are administered in comparison to systemic dosages, but the medication is concentrated at a specific treatment site. Local delivery thus produces fewer side effects and achieves more effective results.

A common technique for local delivery of drugs involves coating a stent or graft with a polymeric material which, in turn, is impregnated with a drug or a combination of drugs. Once the stent or graft is implanted within a cardiovascular system lumen, the drug(s) is released from the polymer for the treatment of the local tissues. U.S. Pat. No. 5,605,696 to Eury et al., U.S. Pat. No. 5,464,650 to Berg, et al., and U.S. Pat. No. 5,700,286 to Tartaglia, et al. provide examples illustrating the use of a polymeric coating for the local delivery of a drug or substance.

Stents are scaffoldings, usually cylindrical or tubular in shape, which are inserted into an anatomical passageway and operate to physically hold open and, if desired, to expand the wall of a passageway. Stents are capable of being crimped onto balloon catheters for insertion through small cavities, positioned in a desired location, and then expanded to a larger diameter. Stents can be either balloon expandable or self-expanding.

Grafts are typically placed in a blood vessel to either replace a diseased segment that has been removed, or to form a bypass conduit through a damaged segment of the vessel wall as is the case with an aneurysm, for example. The graft has a tubular portion which spans the site of the damaged tissue and through which the blood flows. The graft has sections at both ends of the tube that are used to secure the graft to the inside of a vessel wall. The graft also has an outer surface, portions of which are in contact with an inner surface of the blood vessel wall, and an inner surface in contact with the blood flowing through the vessel.

FIG. 1 shows an implantable medical device 10, which may be a stent or graft. Device 10 includes a substrate 12 that may be formed of stainless steel, nickel titanium alloy, or another biocompatible metal. Substrate 12 is covered (usually conformally) by a first layer 14. First layer 14 includes polymer containing a drug 16.

An equation describing the drug release rate per unit area of device 10 is as follows:

$$\Phi(t) = D_p \sum_{n=0}^{\infty} b_n \exp\left(\frac{-\pi^2 D_p t(2n+1)^2}{4T^2}\right) \quad \text{(Equation 1)}$$

$$\left(\frac{-\pi}{2T(2n+1)^n}\right)$$

where $\Phi(t)$=release rate of drug as a function of time, $D_p$=diffusivity of drug 16 in polymer film 14, $\pi$=3.14159, T=thickness of polymer film 14, $$\text{and } b_n = \frac{2}{T} \int_o^T C_o \cos\left\{\frac{\pi x(2n+1)}{2T}\right\} dx$$

where $C_o$ is the concentration of drug in the polymer at time zero.

Equation 1 assumes that: (1) all resistance to drug release is determined by the diffusivity of drug 16 in polymer 14; (2) the concentration of drug 16 is uniform throughout; (3) drug 16 does not go into the metallic surface 12; and (4) drug 16 is rapidly removed from the surface of polymer 14 as soon as drug 16 is released from polymer 14.

The diffusivity of drug 16 in polymer 14, $D_p$, in turn is determined by certain properties of drug 16 (e.g., molecular weight, size) and physical properties of the polymer 14 through which drug 16 is diffusing (e.g., pore size, crystallinity, glass transition temperature, polarity or hydrophobicity).

FIG. 2 illustrates the predicted drug release rate curve for a polymer matrix carrying a drug, such as first layer 14, illustrated in FIG. 1. Curve 8 is an exponentially decreasing curve.

A problem associated with the use of a polymeric coating as a matrix for carrying the drug is that the rate at which the drug is released is highly variable, typically exhibiting a very high rate of release after the medical device is implanted in the patient, followed by a significantly lower rate of release. This may be undesirable in many applications, since the initial concentrations may be too high (causing undesirable side effects or even cell death), the later concentrations may be too low to have any therapeutic effect, and the overall residence time of the drug in the target area may be too short to provide the desired therapeutic effect.

For example, for certain antiproliferative drugs, a residence time of thirty minutes may be all that is required to achieve a permanent effect, while others may take up to two weeks. Where nitrous oxide (NO) is used as the antiproliferative drug, a residence time of four to eight weeks is desirable, but even longer durations up to twelve weeks may be beneficial, depending on the patient.

With respect to anti-inflammatory drugs, a long residence time (e.g., several weeks) is desirable, because the anti-inflammatory drug should be delivered until some amount of healing has occurred. Anti-thrombogenic drugs also may require a long residence time, for example, up to five months, since that much time may be required for a stent to become endothelialized.

Thus, there is a need for a mechanism for controlling the release rate of drugs from implantable medical devices to increase the efficacy of local drug delivery in treating patients.

SUMMARY OF THE INVENTION

The present invention allows for a controlled rate of release of a drug or drugs from a polymer carried on an implantable medical device. The controlled rate of release allows localized drug delivery for extended periods, e.g., weeks to months, depending upon the application. This is especially useful in providing therapy to reduce or prevent cell proliferation, inflammation, or thrombosis in a localized area.

One embodiment of an implantable medical device in accordance with the present invention includes a substrate, which may be, for example, a metal or polymeric stent or graft, among other possibilities. At least a portion of the substrate is coated with a first layer that includes one or more drugs in a polymer carrier. A barrier coating overlies the first layer. The barrier (which may be considered a coating) reduces the rate of release of the drug from the polymer once the medical device has been placed into the patient's body, thereby allowing an extended period of localized drug delivery once the medical device is in situ.

The barrier is necessarily biocompatible (i.e., its presence does not elicit an adverse response from the body), and typically has a thickness ranging from about 50 angstroms to about 20,000 angstroms. It is contemplated that the barrier contains mostly inorganic material. However, some organic compounds (e.g., polyacrylonitrile, polyvinylidene chloride, nylon 6-6, perfluoropolymers, polyethylene terephthalate, polyethylene 2,6-napthalene dicarboxylate, and polycarbonate) may be incorporated in the barrier. Suitable inorganic materials for use within the barrier include, but are not limited to, inorganic elements, such as pure metals including aluminum, chromium, gold, hafnium, iridium, niobium, palladium, platinum, tantalum, titanium, tungsten, zirconium, and alloys of these metals, and inorganic compounds, such as inorganic silicides, oxides, nitrides, and carbides. Generally, the solubility of the drug in the material of the barrier is significantly less than the solubility of the drug in the polymer carrier. Also, generally, the diffusivity of the drug in the material of the barrier is significantly lower than the diffusivity of the drug in the polymer carrier.

The barrier may or may not be biodegradable (i.e., capable of being broken down into harmless compounds by the action of the body). While it is contemplated that non-biodegradable barrier may be preferable, some biodegradable materials may be used as barriers. For example, calcium phosphates such as hydroxyapatite, carbonated hydroxyapatite, tricalcium phosphate, beta-tricalcium phosphate, octacalcium phosphate, amorphous calcium phosphate, and calcium orthophosphate may be used. Certain calcium salts such as calcium phosphate (plaster of paris) may also be used. The biodegradability of the barrier may act as an additional mechanism for controlling drug release from the underlying first layer.

The one or more drugs contained within the polymer may include, but are not limited to, antineoplastic, anti-inflammatory, antiplatelet, anticoagulant, fibrinolytic, thrombin inhibitor, antimitotic, antiallergic, and antiproliferative substances.

In accordance with one embodiment of the present invention, the barrier is a homogeneous layer. A homogeneous layer of barrier may be produced by several methods, depending on the type of materials selected from the barrier. For example, nitride barriers, such as titanium nitride and chromium nitride, may be deposited by cathodic arc physical vapor deposition. Oxide barriers, such as silicon dioxide and aluminum oxide, can be produced by reactive sputtering. Metallic barriers, such as aluminum, gold, tungsten, platinum, or alloys of metals, may be produced by sputtering, thermal evaporation, or electron beam evaporation, as well as electroless deposition.

In accordance with another embodiment of the present invention, the barrier is formed by a number of discrete deposits on the surface of the polymer coating. The release rate of the drug from the polymer coating may be manipulated by controlling the fraction of the surface area covered by the barrier. Such a barrier may be obtained, for example, by cathodic arc sputtering, reactive sputtering, thermal evaporation, and electron beam (e-beam) evaporation of materials such as aluminum, chromium, gold, iridium, niobium, platinum, tantalum, titanium, and tungsten.

In accordance with another embodiment of the present invention, the barrier is intermixed with the first layer at and near the outer surface of the first layer, rather than being a discrete layer atop the first layer. This embodiment may be produced by several techniques, including for example, ion implantation, plasma ion implantation, alkoxide hydrolysis, and electroless deposition. Ion implantation and plasma ion implantation may produce, for example, titanium and palladium barrier coatings. Alkoxide hydrolysis may produce barrier coatings of titanium oxide, zirconium oxide, and aluminum oxide from titanium alkoxides, zirconium alkoxides and aluminum alkoxides, respectively. Electroless deposition may produce, for example, palladium and gold barrier coatings.

These and other embodiments and aspects of the present invention may be better understood in view of the drawings and the following detailed description.

BRIEF DESCRIPTION OF THE DRAWINGS

The use of the same reference numbers in different drawings indicates similar or identical items.

DETAILED DESCRIPTION

Figure 1:
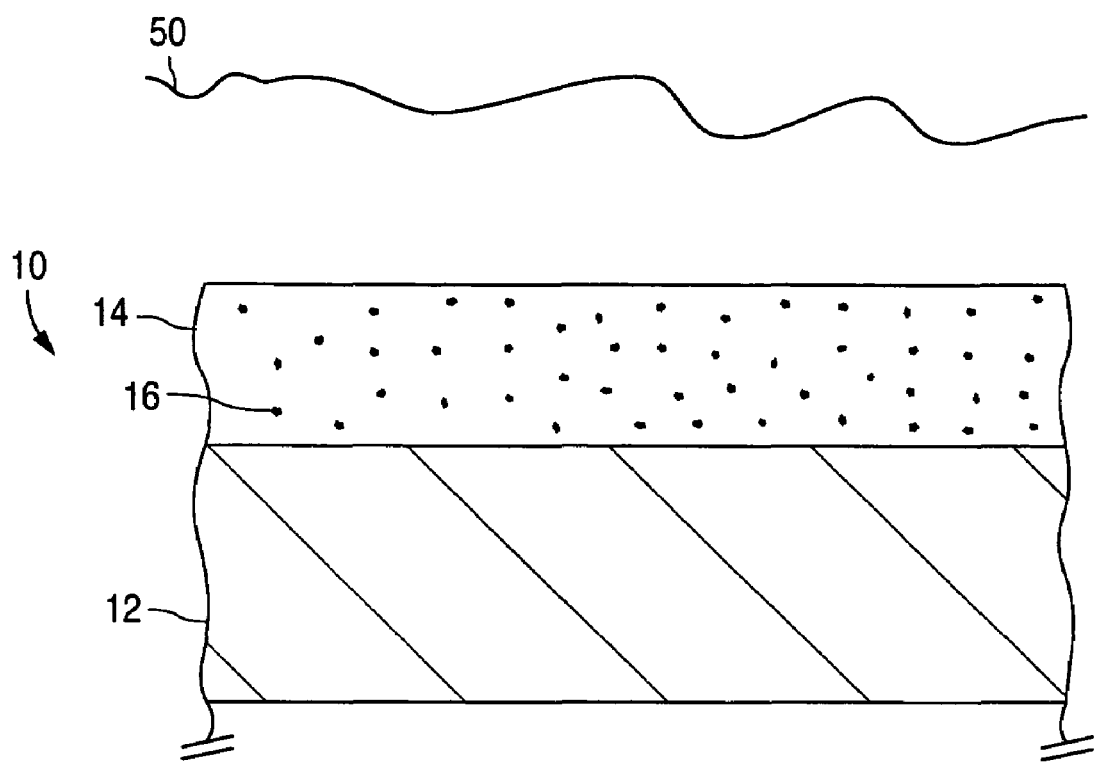
FIG. 1 is a partial cross-sectional view of a conventional implantable medical device having a polymer coating that carries a drug.
Figure 2:
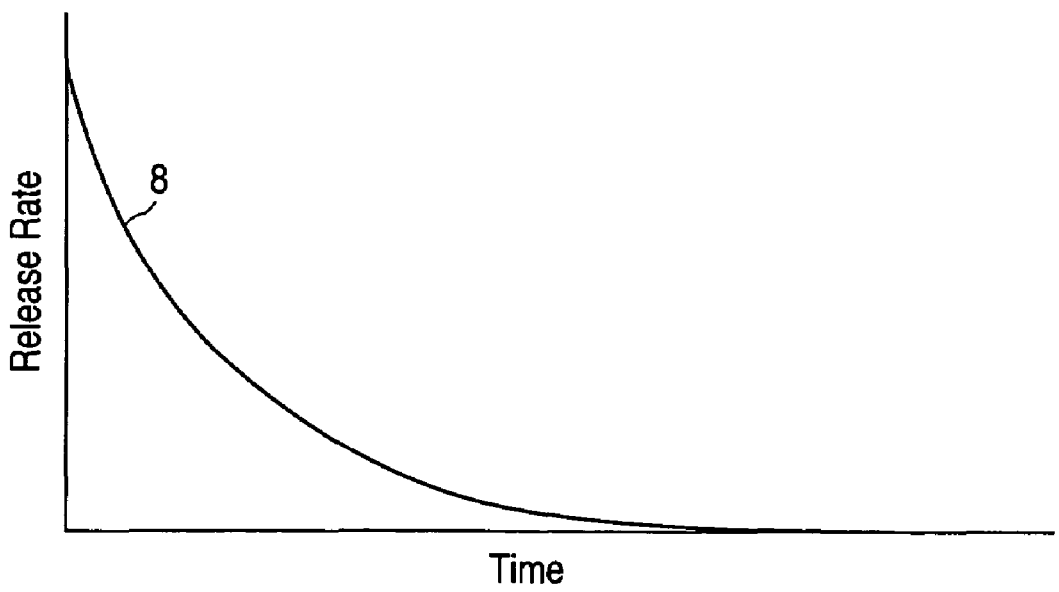
FIG. 2 illustrates a theoretical drug release rate curve for the implantable medical device of FIG. 1.
Figure 3:
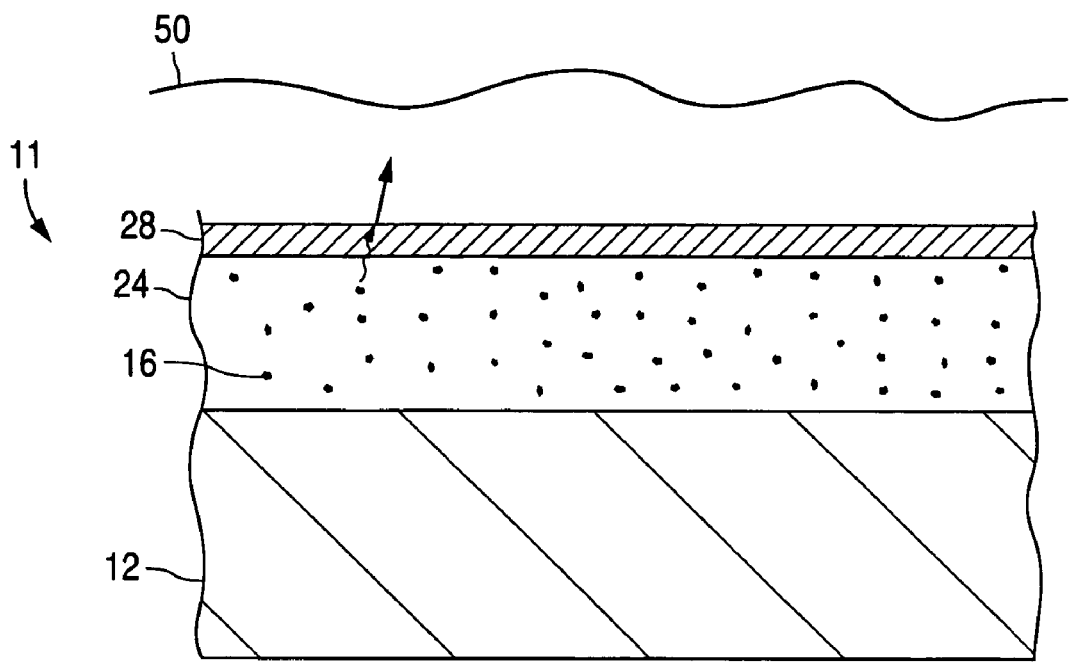
FIG. 3 is a partial cross-sectional view of a barrier on the surface of a polymer-coated implantable medical device in accordance with one embodiment of the present invention.

FIG. 3 is a partial cross-sectional view of implantable medical device 11, which may be a stent or graft, among other possibilities. Medical device 11 includes a substrate 12. A first layer 24 is present on the outer surface of substrate 12. First layer 24 includes a polymer and one or more drugs 16 carried within the polymer. First layer 24 can have a thickness ranging from about 2,000 angstroms to about 200,000 angstroms, or more particularly from about 10,000 angstroms to about 100,000 angstroms. Barrier 28 is present as a homogenous layer on the top surface of first layer 24. Barrier 28 is biocompatible, and typically has a thickness ranging from about 50 angstroms to about 20,000 angstroms, e.g., from about 100 angstroms to about 5,000 angstroms. In this embodiment, barrier 28 is an inorganic material.

Barrier 28 acts to reduce the rate of delivery of drug 16 to internal target tissue area 50 by at least one of two mechanisms. First, the solubility of drug 16 in barrier 28 is substantially less (i.e., at least two to three orders of magnitude less) than the solubility of drug 16 in first layer 24. Likewise, the diffusivity of drug 16 in barrier 28 is significantly lower than the diffusivity of drug 16 in first layer 24. Accordingly, drug 16 will diffuse more slowly through barrier 28 than through first layer 24. Secondly, barrier 28, being mostly an inorganic material, is composed of much smaller molecules than those found within the polymer in first layer 24. The barrier molecules are aligned more tightly and in a more orderly fashion than the polymer molecules, thereby leaving less void space through which drug 16 can travel.

Some barriers, especially defect-free metallic films and $SiO_x$ films, will be very impermeable, except for microfractures through the barrier coating. While these microfractures may link the top and bottom of the barrier coating, the paths of the microfractures linking the top and bottom of the barrier coating are tortuous, and thus the path that drug 16 must take to exit medical device 11 is much longer than the thickness of barrier 28. Moreover, since the drug is restricted to diffusing only through the microfractures, the area available for diffusion is greatly reduced as well.

A simple model for the embodiment illustrated in FIG. 3 holds that the rate of release of drug 16 from barrier 28 per unit area may be expressed by the following equation:

$$\text{Release rate} = \frac{D_f k}{T_I} C_p^o \exp\left(\frac{-D_f k t}{T_P T_I}\right) \quad \text{(Equation 2)}$$

where $D_f$=diffusivity of drug 16 in barrier 28;
$k$=partition coefficient for drug 16 between first layer 24 and barrier 28;
$T_I$=thickness of barrier 28;
$C_p^o$=initial concentration of drug 16 in barrier 28; and
$T_P$=thickness of first layer 24.

This equation assumes that all of the resistance to drug release is in the barrier 28. This is a reasonable assumption since, typically, $D_f$ is at least two to three orders of magnitude lower than the diffusivity of drug 16 in first layer 24. As can be seen from Equation 2, variables $D_f$, k, and $T_f$, are the most significant variables affecting drug release. Of course, the present invention does not depend on this equation or the assumptions discussed above.

Suitable inorganic materials for barrier 28 include, but are not limited to, silicides, oxides, nitrides, and carbides. Suitable silicides may include silicides of vanadium, zirconium, tungsten, titanium, niobium, and tantalum. Suitable oxides may include oxides of aluminum, barium, calcium, hafnium, niobium, silicon, tantalum, titanium, tungsten, and zirconium. Suitable nitrides may include nitrides of chromium, silicon, titanium, and zirconium. Suitable carbides may include carbides of silicon and titanium. Other suitable materials may include molybdenum disulfide, amorphous diamond, diamond-like carbon, pyrolytic carbon, ultra-low temperature isotropic (ULTI) carbon, amorphous carbon, strontium titanate, and barium titanate. Also suitable for use are pure metals, such as aluminum, chromium, gold, hafnium, iridium, niobium, palladium, platinum, tantalum, titanium, tungsten, zirconium, and alloys of these metals.

Several methods may be used to deposit barrier 28 on first layer 24, depending on the application. For example, silicide compounds, such as vanadium disilicide, zirconium disilicide, tungsten disilicide, titanium disilicide, niobium disilicide, tantalum disilicide, vanadium silicide, titanium trisilicide, and tantalum trisilicide may be deposited by sputtering or chemical vapor deposition (CVD).

Oxide barrier coatings, such as tantalum oxide, titanium dioxide, zirconium oxide, niobium oxide, tungsten oxide, aluminum oxide, and silicon dioxide can be produced by reactive sputtering. The power source used in this method may be AC or DC, and utilizes the pure element as a target with a sputter gas of argon and low levels of oxygen.

Nitride barrier coatings, such as titanium nitride, titanium carbo nitride, chromium nitride, titanium aluminum nitride, and zirconium nitride can be deposited on first layer 24 at relatively low temperatures (i.e., less than 60° C.) by cathodic arc vacuum deposition. Such a method may be chosen where first layer 24 and drug 16 are temperature-sensitive.

Films of pure metals (e.g., aluminum, gold, tungsten, platinum) may be produced by physical vapor deposition (PVD) methods such as sputtering, thermal evaporation, or electron beam evaporation. Alloys of these metals can be deposited by sputtering if, for example, an alloy sputtering target is used or multiple metal targets are simultaneously sputtered. Alloys may also be deposited utilizing thermal evaporation or electron beam evaporation if several evaporation sources are used simultaneously.

Suitable polymer materials for first layer 24 can include, but are not limited to, polyurethanes, polyesterurethanes, silicone, fluoropolymers, ethylene vinyl acetate, polyethylene, polypropylene, polycarbonates, trimethylenecarbonate, polyphosphazene, polyhydroxybutyrate, polyhydroxyvalerate, polydioxanone, polyiminocarbonates, polyorthoesters, ethylene vinyl alcohol copolymer, L-polylactide, D,L-polylactide, polyglycolide, polycaprolactone, copolymers of lactide and glycolide, polymethylmethacrylate, poly(n-butyl) methacrylate, polyacrylates, polymethacrylates, elastomers, and mixtures thereof.

Representative elastomers include, but are not limited to, a thermoplastic elastomer material available under the trade name "C-FLEX" from Concept Polymer Technologies of Largo, Fla., polyether-amide thermoplastic elastomer, fluoroelastomers, fluorosilicone elastomer, sytrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile, rubber, polyester, styrene, ethylene, propylene, butadiene and isoprene, polyester thermoplastic elastomer, and mixtures thereof.

The choice of the polymer in first layer 24 typically depends on the selection of the particular drug 16. For a drug 16 that is to be dissolved in the polymer, the factors to be considered in selecting an appropriate polymer include the molecular structure of both the polymer and the drug, the crystallinity or amorphousness of the polymer, the molecular weight of the drug (which is indicative of its size on a molecular level), and the solubility of the drug in the polymer. Examples of drug/polymer pairings include dexamethasone in silicone or polyurethanes or fluoroelastomer; taxol in ethylene vinyl acetate or L-polylactide or polycaprolactone or polyurethanes; rapamycin in polymethylmethacrylate or poly (n-butyl)methacrylate; tranilast in polyurethanes or ethylene vinyl acetate; and fluorouracil in polyurethanes.

Examples of drug 16 include antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol-Myers Squibb Co., Stamford, Conn.). Examples of such antiinflammatory substances include estradiol. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such antiallergic substances include permirolast potassium and tranilast. Examples of such cytostatic or antiproliferative agents include actinomycin D as well as derivatives and analogs thereof (manufactured by Sigma-Aldrich, Milwaukee, Wis.; or COSMEGEN® available from Merck & Co., Inc., Whitehouse Station, N.J.), angiopeptin, mitomycin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J., calcium channel blockers (such as nifedipine), colchicine, fibrolast growth factor (FGF) antagonists, fish oil (omega 3-fatty acid), histamine antagonists, lovastatin (an inhibitor of HMB-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide.

Other drugs or agents that may be used include, for example, alpha-interferon, genetically engineered epithelial cells, and dexamethasone. While the preventative and treatment properties of the foregoing drugs or agents are well-known to those of ordinary skill in the art, the substances or agents are provided by way of example and are not meant to be limiting. Other drugs that may be carried in a polymer coating are equally applicable for use with the present invention.

According to the present invention, the release rate of the drug typically will be controlled in part by the material selected for the barrier. For instance, the barrier material may be an inorganic compound, which is typically polar or ionic in nature. Generally, if the selected drug 16 is likewise polar or ionic in nature (e.g., cisplatin, fluoracil), then the solubility of drug 16 in barrier 28 will be higher, resulting in a higher diffusivity, and thus a faster rate of delivery of drug 16 through barrier 28 to internal target tissue area 50. Conversely, if the selected drug 16 is nonpolar, (e.g., TAXOL®, dexamethasone), then the solubility of drug 16 in barrier 28 will be lower, resulting in a lower diffusivity, and thus a lower rate of delivery of drug 16 through barrier 28 to internal target tissue area 50. However, this is not always the case. Titanium dioxide is a polar inorganic compound, but it has such a high degree of crystallinity, and an affinity for itself that other polar compounds (e.g., the drug to be delivered) do not necessarily dissolve into titanium dioxide very well.

Figure 4:
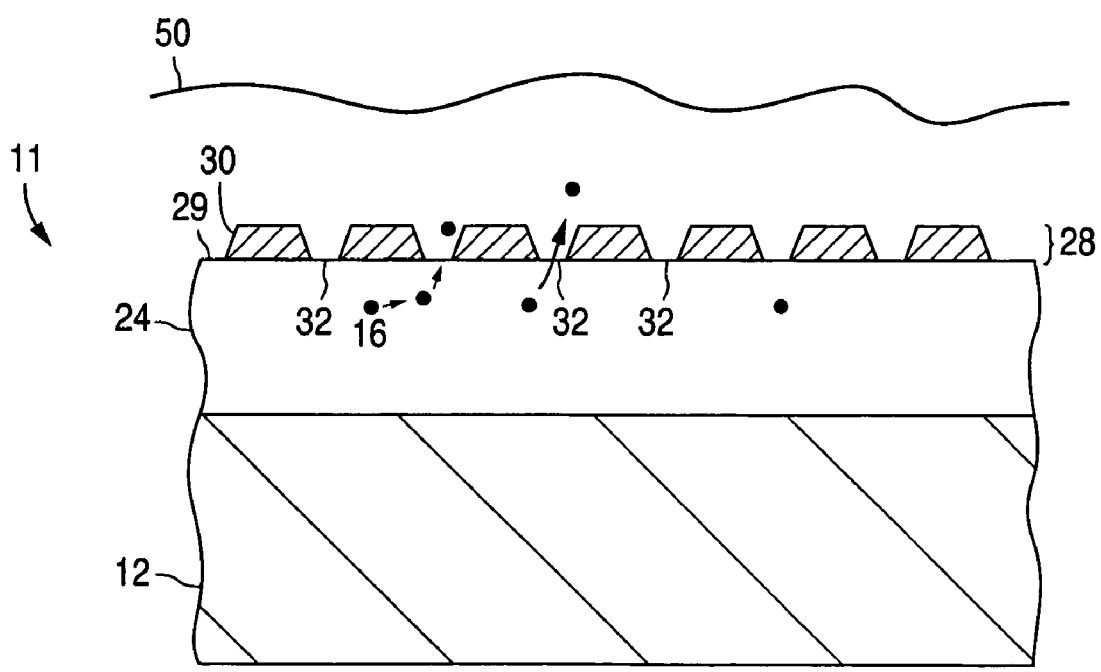
FIG. 4 is a partial cross-sectional view of a barrier on the surface of a polymer-coated implantable medical device in accordance with a second embodiment of the present invention.

FIG. 4 illustrates another embodiment of the present invention, wherein barrier 28 is composed of a number of discrete deposits above first layer 24. When using certain deposition methods, the first few atoms or molecules of barrier 28 deposited on first layer 24 form small nucleation sites 30 on the surface 29 of first layer 24. Barrier 28 may be made discontinuous by arresting the deposition process at the nucleation stage, as illustrated in FIG. 4. However, if the deposition is allowed to continue, nucleation sites 30 expand in surface area and eventually coalesce into a continuous film, as barrier 28 is illustrated in FIG. 3.

In the embodiment illustrated in FIG. 4, the rate of drug delivery from first layer 24 to internal tissue target area 50 is reduced primarily by the presence of nucleation sites 30. Nucleation sites 30 reduce the surface area available for drug 16 to diffuse from first layer 24 toward the internal tissue target area 50, because the vast majority of drug 16 will preferentially diffuse between nucleation sites 30 at spaces 32. While drug 16 may diffuse through nucleation sites 30, it will do so at a much slower rate. Drug 16 situated beneath nucleation site 30 will not proceed directly to tissue 50 through nucleation site 30, but will instead be directed by the diffusion gradient formed toward a space 32. Nucleation sites 30 thus may also increase the length and tortuosity of the average diffusion path taken by molecules of drug 16, again resulting in a slower rate of diffusion of drug 16 from first layer 24.

The release rate associated with the embodiment of FIG. 4 may be generally described by the following equation:

$$\text{Release Rate} = (1-A)\Phi(t) \qquad \text{(Equation 3)}$$

where A=fraction of surface area covered by nucleation sites; and $\Phi(t)$ is as defined in Equation 1.

Equation 3 assumes that there is no diffusion through nucleation sites 30. Again, this equation is provided as an explanatory aid, and does not in any way limit the invention.

Advantageously, in this embodiment, the rate of drug delivery (and thus, the effective treatment time) may be manipulated by controlling the number of nucleation sites 30 that are permitted to form on surface 29 of first layer 24. The number of nucleation sites may be controlled by controlling various deposition process parameters, such as deposition rate, substrate temperature, energy of the deposited atoms, substrate surface cleanliness and defects, angle of the incident atom flux, and substrate surface roughness.

The embodiment illustrated in FIG. 4 may be achieved by performing deposition processes that deposit layers of material by way of nucleation, such as cathodic arc sputtering, reactive sputtering, thermal evaporation and electron beam (e-beam) evaporation of materials such as gold, palladium, and aluminum.

The embodiment illustrated in FIG. 4 may also be achieved by depositing a continuous film, and then creating holes in that film. For example, metal films can be deposited with differing amounts of grain structure. An etching chemical (e.g., typically mixtures of mineral acids) may be used to preferentially etch between grains and remove some of the metal film. Alternately, a continuous film could be deposited, and holes made in that continuous film by, for example, ion milling, a laser, or electron beam machining. Another method for achieving this embodiment would be deposition of a continuous film, followed by mechanically stressing the film, so that the continuous film fractures at preselected locations.

Figure 6:
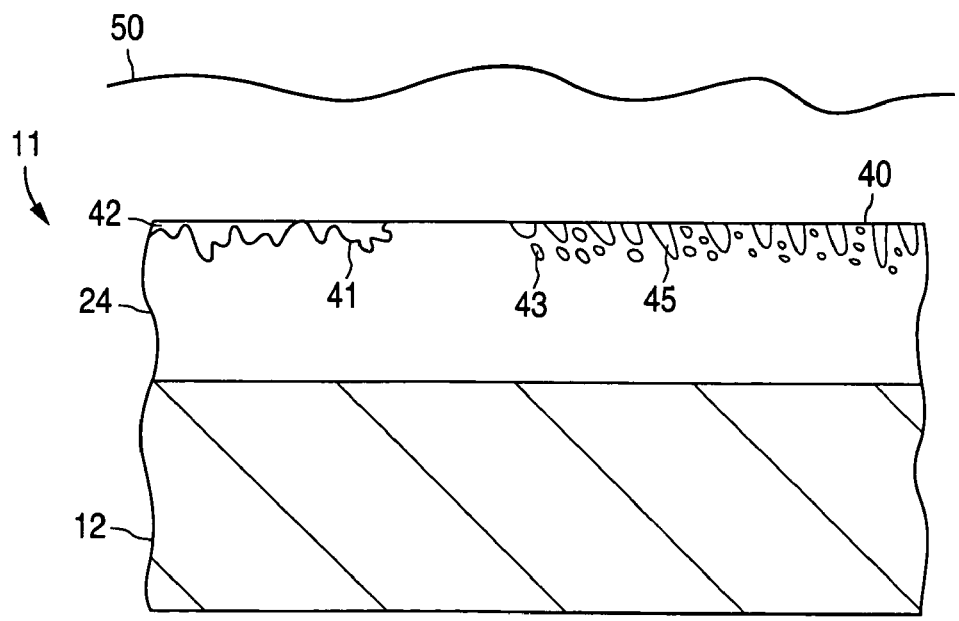
FIG. 6 is a partial cross-sectional view of various types of barriers on or near the surface of an implantable medical device in accordance with a third embodiment of the present invention.

FIG. 6 illustrates another embodiment of the invention, wherein first layer 24, and the barrier coating are not two discrete layers. Instead, the interface between first layer 24 and barrier 40 is irregular, because barrier 40 is blended with first layer 24 to form an intermixed zone 42 at and near the top surface of first layer 24. Intermixing of the barrier 40 with first layer 24 may result when barrier 40 is deposited using one of several methods, whereby the deposited inorganic materials actually penetrate into first layer 24, rather than merely adhering to the surface of first layer 24. These methods include, for example, ion implantation, plasma ion implantation, alkoxide hydrolysis, and electroless deposition. Intermixed zone 42 may include isolated bodies 43 of barrier material formed within first layer 24 and/or fingers 45 of barrier coating material extending into first layer 24.

The rate of drug delivery from first layer 24 to internal target tissue area 50 may be reduced in large part by at least two mechanisms in this embodiment. First, if drug 16 diffuses through the barrier material in intermixed zone 42, then drug 16 may have to follow a more tortuous diffusion path than drug 16 would otherwise follow, decreasing the diffusion rate. Second, if the barrier material in intermixed zone 42 acts as a complete barrier to diffusion, then the area normal to the direction of diffusion is significantly reduced, thus reducing the diffusion rate, in a manner similar to the nucleation sites in the embodiment illustrated in FIG. 4.

Meaningful quantitative or semiquantitative descriptions of drug release rates from the embodiment illustrated in FIG. 6 are difficult to provide, since the geometry of the intermixed zone 42 is highly variable. However, it can be stated that, regardless of the geometry of the intermixed zone, the rate of release of drug 16 from first layer 24 will be significantly reduced.

One of ordinary skill in the art will appreciate that, for all of the embodiments described herein, the thickness of the barrier used may be varied, with a corresponding change in the drug release rate. Generally, the thicker the barrier, the greater the reduction in the drug release rate. However, there is a practical limit on the thickness of the barrier to be applied to first layer 24. If the barrier becomes too thick, then, when subjected to stress from mechanical flexing or changes in temperature, internal stresses will build up within the barrier. When these internal stresses exceed the adhesion between the barrier and the underlying film, the barrier may fracture throughout. Small pieces of the barrier may then be lifted off from first layer 24. The pieces could enter the lumen of a blood vessel, and act as an embolus, with potentially very harmful effects on the patient.

EXAMPLE 1

Use of $SiO_x$ Film as a Barrier Coating to Reduce the Rate of Release of Nitric Oxide from a Polymer Coated Medical Device Healthy endothelial cells located along the intima (the innermost layer of cells lining the blood vessels) produce a nearly constant supply of nitric oxide. Nitric oxide molecules signal the surrounding smooth muscle cells. We currently believe nitric oxide molecules also prevent the smooth muscle cells from migrating and/or proliferating, which, it is postulated, would reduce the incidence of restenosis following PTCA. To be effective in local delivery, nitric oxide would ideally be released over a period of weeks (e.g., four to eight weeks, generally, and in some cases, up to twelve weeks, depending on the patient). In accordance with one embodiment of the invention, a homogeneous film of non-stoichiometric silicon dioxide (known as $SiO_x$) is deposited as barrier coating 28 on first layer 24. First layer 24 contains drug 16, which in this case is nitric oxide or a molecule which releases nitric oxide.

Experimental data collected by others has shown that a polycarbonate film having an average molecular weight in the range of 20,000 to 40,000 g/mole has an oxygen ($O_2$) transmission rate of 1000 $cm^3/m^2$-atm-day. See, Erlat, et al., "Morphology and Gas Barrier Properties of Thin $SiO_x$ Coatings on Polycarbonate: Correlations with Plasma-enhanced Chemical Vapor Deposition Conditions," J. Mater. Res., Vol. 15, No. 3, March 2000. By depositing a $SiO_x$ coating having a thickness of approximately 30 nanometers (nm) on the polycarbonate, using plasma-enhanced chemical vapor deposition, the oxygen transmission rate was reduced by one order of magnitude to approximately 100 $cm^3/m^2$-atm-day. By increasing the thickness of the $SiO_x$ coating deposited to 60 nanometers, the oxygen transmission rate was further reduced by another order of magnitude, to approximately 10 $cm^3/m^2$-atm-day. A less dramatic reduction in oxygen transmission was observed with further increases in $SiO_x$ coating thickness.

Since oxygen ($O_2$) and nitric oxide (NO) are similar to each other in size and molecular weight, we anticipate that an implanted medical device (e.g., a stent or graft) having a $SiO_x$ layer provided atop a polymeric coating containing nitric oxide would cause a similar reduction in the rate at which nitric oxide is released from the polymeric material into a target tissue area. That is, the release rate of nitric oxide from the polymeric carrier could be reduced by a factor of 10 by depositing a $SiO_x$ coating that is 30 nanometers thick on the polymeric carrier, and reduced by a factor of 100 by depositing a $SiO_x$ coating 60 nanometers thick on the polymeric carrier. As a result, for a given mass of nitric oxide loaded into the polymer carrier, the period of time over which nitric oxide is released could be extended by factors of 10 and 100, respectively. Accordingly, the implantable medical device having such a polymer coating and barrier coating would be useful in providing localized drug delivery for an extended period to a patient after PTCA.

EXAMPLE 2

Figure 5:
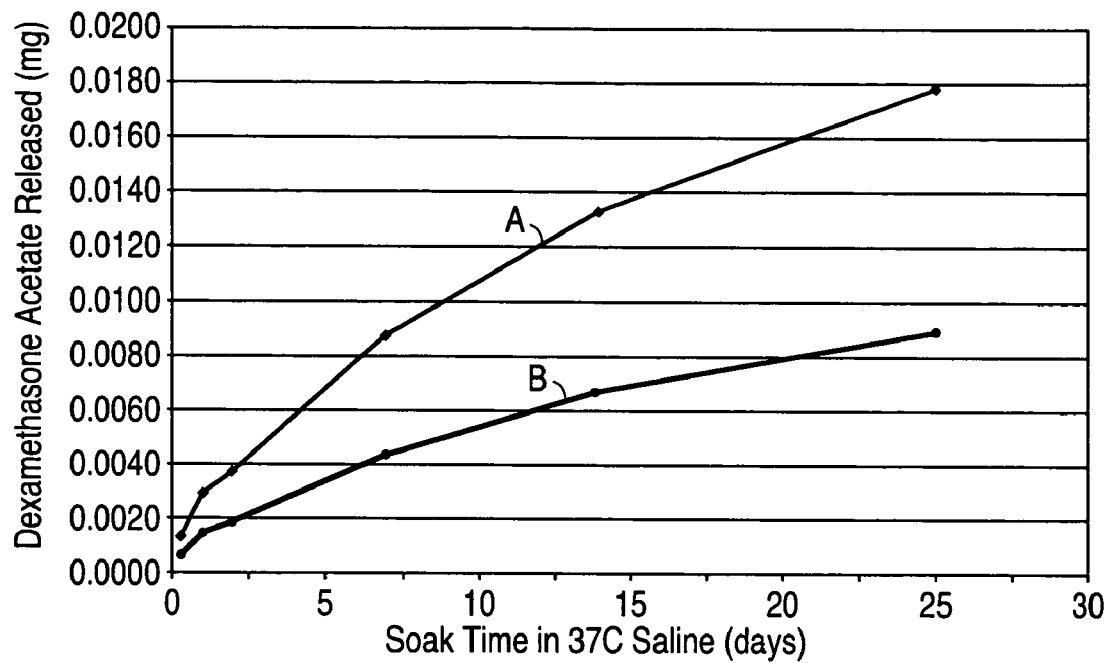
FIG. 5 is a graph depicting the release of dexamethasone acetate from a silicone polymer and the predicted release of dexamethasone acetate when a barrier is applied to the silicone polymer.

Use of Discontinuous Barrier Coating to Reduce the Rate of Release of Dexamethasone from a Silicone Polymer Line A of FIG. 5 illustrates the release of dexamethasone acetate ($C_{22}H_{29}FO_5$), a synthetic steroid used as an antiinflammatory agent, from collars made from a silicone polymer over a period of 25 days when the polymeric collars were immersed in saline solution at a temperature of 37° C. Each polymeric collar was loaded with approximately 0.25 mg of dexamethasone acetate. A total of twenty polymeric collars were tested, and the averaged results are shown. After 25 days, a total of 0.018 mg of dexamethesone had been released, on average, from each polymeric collar.

Assuming nucleation sites 30 of a barrier material were deposited on the silicone polymer in a manner similar to that illustrated in FIG. 4, so as to cover 50% of the available surface area, then the release rate would be reduced by 50%, with the result that the drug release curve would be predicted to appear as shown by line B of FIG. 5. That is, after 25 days, an average of 0.009 mg of dexamethasone would be released. Advantageously, the reduction in the drug release rate by 50% essentially means that the drug would be locally delivered to the body for a period of time twice as long, significantly extending the time of drug release.

Similarly, the process parameters could be controlled so that nucleation sites 30 cover 75% of surface 29 of first layer 24 (which FIG. 4 approximates). This would result in a drug delivery rate that is approximately 25% lower than that associated with the homogeneous film embodiment illustrated in FIG. 3.

EXAMPLE 3

Method for Producing a Titanium Oxide Barrier Coating on a Polymer-Coated Medical Device by Alkoxide Hydrolysis One method by which the embodiment illustrated in FIG. 6 may be produced is alkoxide hydrolysis. If an implantable medical device having a first layer 24 is exposed to a humid environment and then immersed in a metal alkoxide solution, within seconds, metal oxide will be formed at or near the top surface of first layer 24 by reaction of the alkoxide with the water in the polymer coating. As long as the polymer contains some moisture (e.g., at least 1% by weight), the reaction can go forward. Examples of suitable metal alkoxides include titanium ethoxide and titanium propoxide.

A solution of titanium ethoxide is created in dry ethanol at concentrations from about 0.1% to 10%. A polymer coated stent is exposed to an environment with controlled relative humidity between 20% and 100% for between 0.5 and 60 minutes. The stent is then immersed in the alkoxide solution for between 1 and 60 seconds, and then removed. The excess alkoxide solution is rinsed off using ethanol or water. The stent is then dried in a suitable environment (temperature from 20° to 70° C. for 1 to 60 minutes).

EXAMPLE 4

Methods for Producing Barrier Coatings on a Polymer by Electroless Plating

Another method by which the embodiments illustrated in FIGS. 3 and 6 may be produced is reductive deposition in solution, or electroless plating of a material onto a polymer coated surface of an implantable medical device. Electroless plating uses a chemical reduction reaction to deposit metal on a substrate without the passage of an electric current. Non-conductive substrates, such as polymers, are readily plated by this method if the polymer is first catalytically activated. The polymer may be catalytically activated by, for example, immersing it in a colloidal solution containing palladium. This colloidal solution provides nucleation sites of palladium (in this instance) on the polymer prior to electroless deposition of the metal. Certain polymers require an etching step before activation.

Biocompatible inorganic barriers that may be deposited by electroless deposition include palladium (Pd) and gold (Au). Reducing agents for palladium include hypophosphite, amineborane, and hydrazine. Reducing agents for gold include borohydride, amineborane, and hydrazine. The principal reactions that are believed to occur during electroless palladium plating, using hypophosphite as a reducing agent in one commercial application, are shown below.

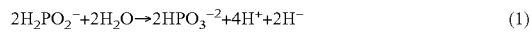

$$2H_2PO_2^- + 2H_2O \rightarrow 2HPO_3^{-2} + 4H^+ + 2H^- \quad (1)$$

$$Pd^{++} + 2H^- \rightarrow Pd^0 + H_2 \quad (2)$$

$$2H_2PO_2^- + 2H^- \rightarrow 2P + 4OH^- + H_2 \quad (3)$$

"Training Course in Electroplating and Surface Finishing," ©1998 by American Electroplaters and Surface Finishers Society, Inc., AESF, 12644 Research Parkway, Orlando, Fla. 32826-3298.

According to the authors, the hypophosphite ion is thought of as being catalytically oxidized (dehydrogenated) on the surface to be plated to release hydride ions ($H^-$) which are then available for reduction of palladium ions at the surface. The products of the reactions are thus the palladium-phosphorus deposit, phosphite ions, hydrogen ions, and hydrogen gas. The phosphorus may be codeposited with palladium to the extent of 1 to 15 percent by weight by a mechanism shown in reaction (3) above.

For example, to provide a palladium barrier coating, an implantable medical device having a polymer coating with a finely etched surface is immersed in an aqueous solution of 5 g/L SnCl₂ and 5 mL/L HCL for a period of about 5 minutes at 35° C. The implantable medical device is then immersed in a plating solution at a temperature of 50° C., the plating solution including 2 g/L of palladium chloride, 160 mL/L of ammonium hydroxide (27%), 26 g/L of ammonium chloride, and 10 g/L of sodium hyposphosphite.

To provide a gold barrier coating, an implantable medical device having a polymer coating with a finely etched surface is immersed in an aqueous solution of 5 g/L SnCl₂ and 5 mL/L HCL for a period of about 5 minutes at 35° C. The implantable medical device is then immersed in a plating solution at a temperature of 75° C., the plating solution including 5.8 g/L of potassium gold cyanide, 13.0 g/L of potassium cyanide, and 21.6 g/L of potassium borohydride.

Codeposition of phosporus and boron may occur in the electroless plating process given above. In another process which is commercially available, a proprietary reducing reagent is used that yields an electroless deposit of pure palladium that is free of phosphorus or boron. The process is known as the Pallatec™ process, and is available from Atotech USA, Inc. of Somerset, N.J. This process reportedly involves the steps of acid cleaning, microetching, activation, and electroless deposition of palladium.

While particular embodiments of the present invention have been shown and described, various changes and modifications can be made without departing from this invention in its broader aspects. For instance, while we have discussed the invention in conjunction with stents and grafts, artisans will appreciate that the invention may be used with any implantable medical device that can be used in conjunction with a drug-loaded polymer for localized drug delivery. For example, such barrier coatings may be applied to drug-loaded polymer coatings on catheters, cerebrospinal fluid shunts, drug delivery pacemaker leads, defibrillation electrodes, artificial hips and bones, breast implants, and other implanted devices. Therefore, the appended claims are to encompass within their scope all such changes and modifications as fall within the true spirit and scope of this invention.

What is claimed is:

1. An implantable medical device, comprising:
   a substrate adapted to be implanted at a site in need of therapy;
   a polymeric layer comprising poly(methylmethacrylate) or poly(butylmethacrylate) supported by the substrate, the polymeric layer containing rapamycin for administering rapamycin to the site in need of therapy by diffusing through the polymeric layer to the site; and
   a barrier over at least a portion of the polymeric layer to reduce the rate of release of rapamycin from the implantable medical device.

2. The implantable medical device of claim 1, wherein the barrier degrades.

3. The implantable medical device of claim 1, wherein the polymeric layer additionally includes poly(ethylene co-vinyl acetate).

4. The implantable medical device of claim 1, wherein the device is a stent.

5. A method of making an implantable medical device, the method comprising:
   forming a coating on the device, wherein the coating comprises poly(butyl methacrylate), rapamycin and poly(ethylene co-vinyl acetate); and
   forming a barrier layer for reducing a rate of release of rapamycin after implantation of the device into a body of a patient.

6. The method of claim 5, wherein the coating is formed by applying a plurality of layers of poly(butyl methacrylate), rapamycin and poly(ethylene co-vinyl acetate) to the device.

7. The method of claim 5, wherein the device is a stent.

8. The implantable medical device of claim 1, wherein the barrier comprises a polymer.

9. The implantable medical device of claim 1, wherein the barrier comprises an inorganic material.

10. The implantable medical device of claim 3, wherein the barrier comprises a polymer and wherein the polymeric layer includes poly(butylmethacrylate).

11. The implantable medical device of claim 10, wherein the device is a stent.

12. The implantable medical device of claim 10, wherein the barrier is a homogeneous layer.

13. The implantable medical device of claim 1, wherein the barrier comprises a polymer; wherein the polymeric layer consists of poly(butylmethacrylate), poly(ethylene co-vinyl acetate), and rapamycin; and wherein the device is a stent.

14. The implantable medical device of claim 1, wherein the barrier comprises a metallic material.

15. The method of claim 5, wherein the barrier layer comprises a polymer.

16. The method of claim 5, wherein the barrier layer comprises a polymer and the device is a stent.

17. The method of claim 16, wherein the barrier layer is blended into the coating.

18. The method of claim 5, wherein the barrier layer comprises an inorganic material.

* * * * *